US012595254B2

(12) United States Patent
Chen et al.

(10) Patent No.: US 12,595,254 B2
(45) Date of Patent: Apr. 7, 2026

(54) CRYSTAL FORM OF RESMETIROM, PREPARATION METHOD THEREFOR, AND USE THEREOF

(71) Applicant: CRYSTAL PHARMACEUTICAL (SUZHOU) CO., LTD., Suzhou (CN)

(72) Inventors: Minhua Chen, Suzhou (CN); Chunxiang Huang, Suzhou (CN)

(73) Assignee: CRYSTAL PHARMACEUTICAL (SUZHOU) CO., LTD., Suzhou (CN)

( * ) Notice: Subject to any disclaimer, the term of this patent is extended or adjusted under 35 U.S.C. 154(b) by 485 days.

(21) Appl. No.: 18/044,717

(22) PCT Filed: Aug. 30, 2021

(86) PCT No.: PCT/CN2021/115205
§ 371 (c)(1),
(2) Date: Mar. 9, 2023

(87) PCT Pub. No.: WO2022/052822
PCT Pub. Date: Mar. 17, 2022

(65) Prior Publication Data

US 2023/0416234 A1 Dec. 28, 2023

(30) Foreign Application Priority Data

Sep. 10, 2020 (CN) ......................... 202010948981.8

(51) Int. Cl.
*C07D 403/12* (2006.01)

(52) U.S. Cl.
CPC ........ *C07D 403/12* (2013.01); *C07B 2200/13* (2013.01)

(58) Field of Classification Search
CPC .......................... C07D 403/12; C07B 2200/13
See application file for complete search history.

(56) References Cited

U.S. PATENT DOCUMENTS 7,452,882 B2 11/2008 Haynes et al.
7,807,674 B2 10/2010 Haynes et al.
(Continued)

FOREIGN PATENT DOCUMENTS

CN 101228135 7/2008
CN 105008335 12/2018
(Continued)

OTHER PUBLICATIONS

Ashizawa, Kazuhide. *Crystal Analysis Science of Polymorphism in Pharmaceuticals*. Maruzen Planet Co., Ltd., 2002, pp. 56-102, 304-317 (English translation of relevant parts provided).
(Continued)

*Primary Examiner* — Kortney L. Klinkel
*Assistant Examiner* — Jackson J Hernandez
(74) *Attorney, Agent, or Firm* — MagStone Law, LLP; Enshan Hong

(57) ABSTRACT

The present invention relates to a new crystal form of Resmetirom (referred to as "Compound I") and a preparation method therefor, a pharmaceutical composition comprising the crystal form, and a use of the crystal form in preparing a THR-β selective agonist drug and a drug for treating NASH and HeFH. Compared with the prior art, the provided crystal form of the compound I has one or more improved properties, solves problems existing in the prior art, and has a great value for the optimization and development of drugs containing the compound I.
(Continued)

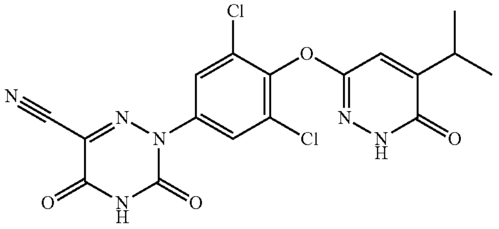

(I)

10 Claims, 5 Drawing Sheets

(56) References Cited

U.S. PATENT DOCUMENTS

| | | | |
|---|---|---|---|
| 9,266,861 | B2 | 2/2016 | Hester et al. |
| RE46,024 | E | 6/2016 | Haynes et al. |
| 9,968,612 | B2 | 5/2018 | Taub et al. |
| 10,376,517 | B2 | 8/2019 | Taub et al. |
| 10,894,050 | B2 | 1/2021 | Hester, II et al. |
| 11,090,308 | B2 | 8/2021 | Taub |
| 2009/0005383 | A1 | 1/2009 | Haynes et al. |
| 2015/0203473 | A1 | 7/2015 | Hester, II et al. |
| 2016/0243126 | A1 | 8/2016 | Taub et al. |
| 2019/0381053 | A1 | 12/2019 | Taub et al. |
| 2020/0230146 | A1 | 7/2020 | Taub |
| 2020/0354345 | A1 | 11/2020 | Vandyck et al. |
| 2021/0122740 | A1 | 4/2021 | Mirmehrabi et al. |
| 2021/0161904 | A1 | 6/2021 | Hester, II et al. |
| 2022/0372021 | A1 | 11/2022 | Chen et al. |

FOREIGN PATENT DOCUMENTS

| | | |
|---|---|---|
| CN | 110167557 | 8/2019 |
| WO | WO 2019242766 | 12/2019 |
| WO | WO 2020010068 | 1/2020 |
| WO | WO 2020227549 | 11/2020 |
| WO | WO 2021078274 | 4/2021 |
| WO | WO 2021/129465 | 7/2021 |
| WO | WO 2022086894 | 4/2022 |
| WO | WO 2022165227 | 8/2022 |
| WO | WO 2022171200 | 8/2022 |

OTHER PUBLICATIONS

Hirayama, Noriaki. *Organic Compound Crystallization Handbook and Principles*. Maruzen, 2008, pp. 17-23, 37-40, 45-51, 57-65 (English translation of relevant parts provided).

Office Action issued in corresponding Japanese Application No. 2023-515709, dated Feb. 18, 2025 (English Translation provided).

Kelly, M. et al. "Discovery of 2-[3, 5-Dichloro-4-(5-isopropyl-6-oxo-1, 6-dihydropyridazin-3-yloxy)phenyl]-3, 5-dioxo-2, 3,4, 5-tetrahydro[1, 2, 4]traiazine-6-carbonitrile (MGL-3196), a Highly Selective Thyroid Hormone Receptor β Agonist in Clinical Trials for the Treatment of Dyslipidemia" *Journal of Medicinal Chemistry*, vol. 57, pp. 3913-3923, Apr. 8, 2014.

International Search Report and Written Opinion issued in corresponding International Application PCT/CN2021/115205 mailed Nov. 25, 2021.

CRYSTAL FORM OF RESMETIROM, PREPARATION METHOD THEREFOR, AND USE THEREOF

CROSS REFERENCE TO RELATED APPLICATIONS

The present application is a national phase application under 35 U.S.C. § 371 of International Application No. PCT/CN2021/115205, filed Aug. 30, 2021, which claims the benefit of priority to Chinese Patent Application No. 202010948981.8 filed with the State Intellectual Property Office of People's Republic of China on Sep. 10, 2020, each of which are incorporated herein by reference in their entirety.

TECHNICAL FIELD

The present disclosure pertains to the field of chemical crystallography, particularly relates to novel crystalline forms of Resmetirom, preparation method and use thereof.

BACKGROUND

Heterozygous familial hypercholesterolemia (HeFH) is the most serious lipid metabolism disorder, which could lead to various life-threatening cardiovascular complications. Nonalcoholic steatohepatitis (NASH) is a severe liver disease with steatosis associated with inflammation and hepatocellular injury. As a selective agonist of thyroid hormone receptor THR-β, Resmetirom can improve the symptoms of NASH and HeFH by reducing the levels of low-density lipoprotein cholesterol, triglyceride and liver fat, and stimulating liver mitochondrial biogenesis in NASH individuals. Resmetirom achieves positive results in phase II trials of NASH and HeFH.

The chemical name of Resmetirom is 2-(3,5-dichloro-4-((5-isopropyl-6-oxo-1,6-dihydropyridazin-3-yl)oxy)phenyl)-3,5-dioxo-2,3,4, 5-tetrahydro-1,2,4-triazine-6-carbonitrile (Referred to as Compound I), and the structure is shown as the follows:

Compound I

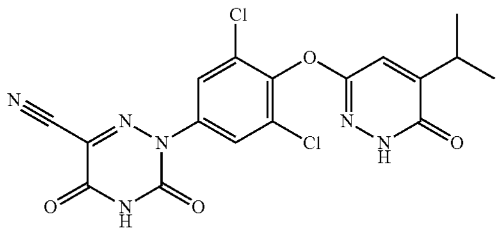

A crystalline form is a solid material whose constituents are arranged in a highly ordered microscopic structure, forming a crystal lattice that extends in all directions. Polymorphism refers to the phenomenon that a compound exists in more than one crystalline form. Compounds may exist in one or more crystalline forms, but their existence and characteristics cannot be predicted with any certainty. Different crystalline forms of drug substances have different physicochemical properties, which can affect drug's in vivo dissolution and absorption and will further affect drug's clinical efficacy and safety to some extent. In particular, for some poorly soluble oral solid or semi-solid dosage forms, crystalline forms can be crucial to the performance of drug product. In addition, the physiochemical properties of a crystalline form are very important to the manufacturing process. Therefore, polymorphism is an important part of drug research and drug quality control. Hydrate, anhydrate form I, methyl isobutyl ketone solvate, and dimethylacetamide solvate of Compound I were disclosed in prior art U.S. Pat. No. 9,266,861B2. According to the guidelines of ICH on the classification of solvents, methyl isobutyl ketone and dimethylacetamide are both Class II solvents which are severely toxic with restricted use, and are not suitable for medicinal use. U.S. Pat. No. 9,266,861B2 disclosed that the purity of Compound I hydrate was only 96.4% (HPLC). The high impurity content will cause changes in the appearance of the drug, affect the stability of the drug, and increase the toxicity and side effects.

Various crystalline forms of compound I such as calcium salt, magnesium salt, sodium salt, potassium salt, and ethanolamine salt were disclosed in WO2020010068A1. At the same time, 27 free crystalline forms of Compound I, including various solvates (such as methanol solvate, acetone solvate, tetrahydrofuran solvate, methyl isobutyl ketone solvate, acetonitrile solvate, dimethyl sulfoxide solvate, dimethylacetamide solvate) and multiple desolvates were also disclosed. According to the content of WO2020010068A1 and the experimental study of the inventors of the present disclosure, the crystalline form A and the crystalline form I disclosed in U.S. Pat. No. 9,266,861B2 are the same crystalline form, the desolvate crystalline form F has a high hygroscopicity, and the desolvate crystalline form S+T, crystalline form V, crystalline form W, and crystalline form Z are all mixture that are composed of non-single crystalline forms.

Crystalline form I is a known solid form of Compound I with better properties, but it needs to be prepared from specific starting materials, such as methyl isobutyl ketone solvate and dimethylacetamide solvate. The inventors of the present disclosure repeated the preparation method disclosed in U.S. Pat. No. 9,266,861B2 to obtain the crystalline form I, and further evaluated the properties of the crystalline form I. The results show that the crystalline form I has low solubility, poor grinding stability as most of the crystalline form I transform to amorphous after grinding, poor compressibility and very poor flowability. Therefore, a single crystalline form of Compound I with high solubility, good physicochemical stability, safety and non-toxicity, and good physicochemical properties is still needed for the development of drugs containing Compound I.

The inventors of the present disclosure have carried out numerous experimental studies on Compound I and try to obtain a more suitable crystalline form for drug use. More than 300 experiments have been carried out, but most obtained are solvates of Compound I, such as methanol solvate, acetone solvate, tetrahydrofuran solvate, chlorobenzene solvate, toluene solvate, cyclohexanone solvate, etc. The inventors of the present disclosure found that Compound I is very easy to combine with solvent to form a solvate, and it is very difficult to obtain a stable and non-solvated single crystalline form.

The inventors of the present disclosure surprisingly discovered crystalline form CSVI of Compound I, which have advantages in at least one aspect of solubility, hygroscopicity, purification ability, stability, adhesiveness, compressibility, flowability, in vitro and in vivo dissolution, bioavailability, etc. In particular, the crystalline forms of the Compound I of the present disclosure have advantages such as high solubility, good physicochemical stability, good mechanical stability, weak hygroscopicity, good flowability, good compressibility, low adhesiveness and good drug product stability, which solves the problems existing in the prior arts and is of great significance for the development of drugs containing Compound I.

SUMMARY

The present disclosure is to provide novel crystalline forms of Compound I, preparation method and pharmaceutical compositions comprising the crystalline forms.

According to the objective of the present disclosure, crystalline form CSVI of Compound I is provided (hereinafter referred to as Form CSVI).

In one aspect provided herein, the X-ray powder diffraction pattern of Form CSVI comprises characteristic peaks at 2θ values of 9.6°±0.2°, 10.1°±0.2°, and 18.9°±0.2° using CuKα radiation.

Furthermore, the X-ray powder diffraction pattern of Form CSVI comprises one or two or three characteristic peaks at 2θ values of 11.6°±0.2°, 19.5°±0.2°, and 23.3°±0.2° using CuKα radiation. Preferably, the X-ray powder diffraction pattern of Form CSVI comprises characteristic peaks at 2θ values of 11.6°±0.2°, 19.5°±0.2°, and 23.3°±0.2° using CuKα radiation.

Furthermore, the X-ray powder diffraction pattern of Form CSVI comprises one or two or three characteristic peaks at 2θ values of 13.7°±0.2°, 20.6°±0.2°, and 31.9°±0.2° using CuKα radiation. Preferably, the X-ray powder diffraction pattern of Form CSVI comprises characteristic peaks at 2θ values of 13.7°±0.2°, 20.6°±0.2°, and 31.9°±0.2° using CuKα radiation.

In another aspect provided herein, the X-ray powder diffraction pattern of Form CSVI comprises at least three characteristic peaks at 2θ values of 9.6°±0.2°, 10.1°±0.2°, 11.6°±0.2°, 18.9°±0.2°, 19.5°±0.2°, 23.3°±0.2°, 13.7°±0.2°, 20.6°±0.2°, 31.9°±0.2°, 6.5°±0.2°, 16.2°±0.2°, 21.9°±0.2°, 24.1°±0.2°, 24.8°±0.2°, 25.7°±0.2°, 26.7°±0.2°, 27.3°±0.2° and 31.1°±0.2° using CuKα radiation.

Without any limitation being implied, the X-ray powder diffraction pattern of Form CSVI is substantially as depicted in FIG. 1.

Without any limitation being implied, the Thermo Gravimetric Analysis (TGA) curve of Form CSVI is substantially as depicted in FIG. 2, which shows 0.2% weight loss when heated to 250° C.

Without any limitation being implied, the weight gain of Form CSVI at 25° C./80% RH is indicating that Form CSVI is non or almost non hygroscopic. The Dynamic Vapor Sorption (DVS) plot of Form CSVI is substantially as depicted in FIG. 3.

Without any limitation being implied, Form CSVI is an anhydrate.

According to the objective of the present disclosure, a process for preparing Form CSVI is also provided. The process comprises:

method 1: adding Compound I into a nitrile or a solvent mixture of nitrile and water, stirring, separating and drying to obtain Form CSVI; or method 2: dissolving Compound I into a solvent mixture of a nitrile and water or a solvent mixture of a nitrile and an alcohol, filtering, cooling the filtrate and stirring to obtain solid, separating and drying to obtain Form CSVI.

Furthermore, in method 1, said nitrile is preferably acetonitrile, the volume ratio of acetonitrile and water in the solvent mixture is preferably 95:5; in method (2), said nitrile is preferably acetonitrile, said alcohol is preferably isopropanol, the volume ratio of acetonitrile and water in the solvent mixture is preferably 95:5, the volume ratio of acetonitrile and isopropanol in the solvent mixture is preferably 1:1.

Furthermore, in method 1, said stirring temperature is preferably −20° C.-76° C., further preferably −20° C.-30° C.; said drying temperature is preferably 10° C.-70° C., further preferably 10° C.-40° C.

Furthermore, in method 1, said dissolving temperature is preferably 40° C.-76° C.; said cooling temperature is preferably −20° C.-5° C., further preferably −20° C.; said drying temperature is preferably 10° C.-70° C., further preferably 10° C.-40° C.

According to the objective of the present disclosure, the present disclosure also provides the use of Form CSVI for preparing other crystalline forms, or salts of Compound I.

According to the objective of the present disclosure, a pharmaceutical composition is provided, said pharmaceutical composition comprises a therapeutically effective amount of Form CSVI and pharmaceutically acceptable excipients.

Furthermore, according to the objective of the present disclosure, Form CSVI can be used for preparing THR-β selective agonist drugs.

Furthermore, according to the objective of the present disclosure, Form CSVI can be used for preparing drugs treating NASH and HeFH.

Form CSVI of the present disclosure has the following advantages:

(1) Compared with prior arts, Form CSVI has a higher solubility. Particularly in SGF, the solubility of Form CSVI is about 2 times that of Form I in the prior art.

Compound I is a poorly water-soluble drug. Higher solubility of Form CSVI drug substance provided by the present disclosure is beneficial to improve drug's in vivo absorption and bioavailability. In addition, drug dose reduction without affecting efficacy is possible due to higher solubility, thereby reducing the drug's side effects and improving drug safety.

(2) Compared with prior arts, Form CSVI has lower hygroscopicity. The test results show that the weight gains of Form I in the prior art is about 2 times that of Form CSVI.

In one aspect, poor hygroscopicity tends to cause chemical degradation and polymorph transformation, which directly affects the physicochemical stability of the drug substance. In addition, poor hygroscopicity will reduce the flowability of the drug substance, thereby affecting the processing of the drug substance.

In another aspect, drug substance with poor hygroscopicity requires low humidity environment during production and storage, which puts strict requirements on production and imposes higher costs. More importantly, poor hygroscopicity is likely to cause variation in the content of active pharmaceutical ingredients in the drug product, thus affecting drug product quality.

(3) Compared with prior arts, Form CSVI of the present disclosure has better compressibility. Failure in hardness/friability test and tablet crack issue can be avoided due to better compressibility, making the preparation process more reliable, improving product appearance, promoting product quality and production efficiency.

(4) Compared with prior arts, Form CSVI of the present disclosure shows low adhesiveness. Adhesiveness evaluation results indicate that adhesion quantity of Form I in the prior art is 5 times that of Form CSVI. Low adhesiveness can reduce the agglomeration of drug substance and effectively improve the adhesion to roller and tooling during dry-granulation and compression process. It is conducive to the dispersion of drug substance with excipients and improving the blend uniformity of the mixing of materials, which ultimately improves product quality.

(5) From CSVI drug substance of the present disclosure has good physicochemical stability. Crystalline state of Form CSVI drug substance doesn't change for at least 6 months when stored under the condition of 25° C./60% RH with open and sealed package. The chemical purity is above 99.7% and remains substantially unchanged during storage. After Form CSVI is mixed with the excipients to form a drug product and stored under the condition of 25° C./60% RH, crystalline state of Form CSVI drug product doesn't change for at least 3 months. The chemical purity remains substantially unchanged during storage. These results show that Form CSVI drug substance has good stability under long term conditions both itself and in drug product, which is beneficial to the drug storage.

Meanwhile, Crystalline state of Form CSVI drug substance doesn't change for at least 6 months when stored under the condition of 40° C./75% RH with open and sealed package. The chemical purity is above 99.7% and remains substantially unchanged during storage. After Form CSVI is mixed with the excipients to form a drug product and stored under the condition of 40° C./75% RH, crystalline state of Form CSVI drug product doesn't change for at least 3 months. The chemical purity remains substantially unchanged during storage. These results show that Form CSVI drug substance has good stability under accelerated conditions both itself and in drug product. Good stability under accelerated conditions is of great importance to the drug development. Drug substance and drug product would go through high temperature and high humidity conditions caused by different season, regional climate and environment during storage, transportation, and manufacturing processes. Therefore, drug substance with good stability under accelerated conditions is of great importance to the drug development. Form CSVI drug substance has good stability under stress condition both itself and in drug product, which is beneficial to avoid the impact on drug quality due to crystal transformation or decrease in purity during drug storage.

(6) Form CSVI of the present disclosure has good physical stability under mechanical force. The crystalline form of Form CSVI doesn't change after grinding. Grinding and pulverization are often required in the drug manufacturing process. Good physical stability of the drug substance can reduce the risk of crystallinity decrease and crystal transformation during the drug production process. Form CSVI has good physical stability under different pressures, which is beneficial to keep crystalline form unchanged during tableting process.

Good physical and chemical stability of drug substance ensure that no crystal transformation or impurities is generated during production and storage. Form CSVI has good physical and chemical stability, ensuring consistent and controllable quality of the drug substance and drug product, minimizing quality change, bioavailability change and toxicity due to crystal transformation or impurity generation.

DETAILED DESCRIPTION

Figure 1:
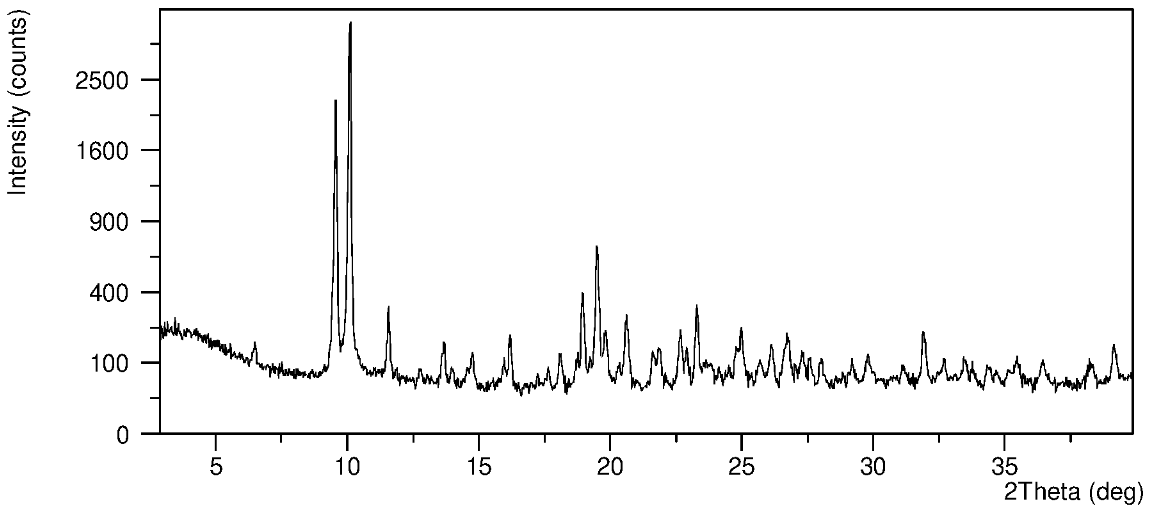
FIG. 1 shows an XRPD pattern of Form CSVI according to example 1

The present disclosure is further illustrated by the following examples which describe the preparation and use of the crystalline forms of the present disclosure in detail. It is obvious to those skilled in the art that changes in the materials and methods can be accomplished without departing from the scope of the present disclosure.

The abbreviations used in the present disclosure are explained as follows:

XRPD: X-ray Powder Diffraction

TGA: Thermo Gravimetric Analysis

DVS: Dynamic Vapor Sorption $^1H$ NMR: Proton Nuclear Magnetic Resonance

HPLC: High Performance Liquid Chromatography

BCS: The Biopharmaceutics Classification System

RH: Relative Humidity

ICH: The International Council for Harmonisation of Technical Requirements for Pharmaceuticals for Human Use Instruments and methods used for data collection:

X-ray powder diffraction patterns in the present disclosure were acquired by a Bruker D2 PHASER X-ray powder diffractometer. The parameters of the X-ray powder diffraction method of the present disclosure are as follows:

X-Ray source: Cu, Kα

Kα1 (Å): 1.5406; Kα2 (Å): 1.54439

Kα2/Kα1 intensity ratio: 0.50

Voltage: 30 (kV)

Current: 10 (mA)

Scan range (2θ): from 3.0 degree to 40.0 degree

Thermo gravimetric analysis (TGA) data in the present disclosure were acquired by a TA Q500. The parameters of the TGA method of the present disclosure are as follows:

Heating rate: 10° C./min

Purge gas: N2

Dynamic Vapor Sorption (DVS) was measured via an SMS (Surface Measurement Systems Ltd.) intrinsic DVS instrument. The instrument control software is DVS-Intrinsic control software. Typical Parameters for DVS test are as follows:

Temperature: 25° C.

Gas and flow rate: $N_2$, 200 mL/min

RH range: 0% RH to 95% RH

Proton nuclear magnetic resonance spectrum data ($^1H$ NMR) were collected from a Bruker Avance II DMX 400M Hz NMR spectrometer. 1-5 mg of sample was weighed and dissolved with 0.5 mL of deuterated dimethyl sulfoxide to obtain a solution with a concentration of 2-10 mg/mL.

The parameters of related substance detection in the present disclosure are shown in Table 1.

TABLE 1

| | | |
|---|---|---|
| Instrument | Waters ACQUITY UPLC H-Class plus with PDA detector | |
| Column | Waters ACQUITY UPLC BEH C18, 2.1 mm*50 mm, 1.7 μm | |
| Mobile phase | A: 0.1% Trifluoroacetic acid in $H_2O$<br>B: 0.1% Trifluoroacetic acid in Acetonitrile | |
| Gradient | Time (min) | % B |
| | 0.00 | 10 |
| | 0.50 | 10 |
| | 2.50 | 50 |
| | 6.50 | 90 |
| | 8.00 | 90 |
| | 8.10 | 10 |
| | 10.00 | 10 |
| Run time | 10 min | |
| Post time | 0 min | |
| Flow rate | 0.5 mL/min | |
| Injection volume | 1 μL | |
| Detector wavelength | 215 nm | |
| Column temperature | 40° C. | |
| Sample temperature | Room Temperature | |
| Diluent | Acetonitrile: $H_2O$ = 50:50 (v/v) | |

The parameters of solubility detection in the present disclosure are shown in Table 2.

TABLE 2

| | | |
|---|---|---|
| Instrument | Agilent1290 with DAD detector | |
| Column | Waters ACQUITY UPLC BEH C18, 50 × 2.1 mm, 1.7 μm | |
| Mobile phase | A: 0.1% Trifluoroacetic acid in $H_2O$<br>B: 0.1% Trifluoroacetic acid in Acetonitrile | |
| Gradient | Time (min) | % B |
| | 0.00 | 10 |
| | 0.50 | 10 |
| | 2.50 | 50 |
| | 6.50 | 90 |
| | 8.00 | 90 |
| | 8.10 | 10 |
| | 10.00 | 10 |
| Run time | 10 min | |
| Post time | 0 min | |
| Flow rate | 0.5 mL/min | |
| Injection volume | 1 μL | |
| Detector wavelength | 215 nm | |
| Column temperature | 40° C. | |
| Sample temperature | Room Temperature | |
| Diluent | Acetonitrile: $H_2O$ = 50:50 (v/v) | |

In the present disclosure, said "stirring" is accomplished by using a conventional method in the field such as magnetic stirring or mechanical stirring and the stirring speed is 50 to 1800 r/min. Preferably the magnetic stirring speed is 300 to 900 r/min and mechanical stirring speed is 100 to 300 r/min.

Said "separation" is accomplished by using a conventional method in the field such as centrifugation or filtration. The operation of "centrifugation" is as follows: the sample to be separated is placed into the centrifuge tube, and then centrifuged at a rate of 10000 r/min until the solid all sink to the bottom of the tube.

Said "drying" is accomplished by using a conventional method in the field such as vacuum drying, blast drying or free-air drying. The drying temperature can be room temperature or higher. Preferably the drying temperature is from room temperature to about 60° C., or to 50° C., or to 40° C. The drying time can be 2 to 48 hours, or overnight. Drying is accomplished in a fume hood, forced air convection oven or vacuum oven.

Said "characteristic peak" refers to a representative diffraction peak used to distinguish crystals, which usually can have a deviation of ±0.2° using CuKα radiation.

In the present disclosure, "crystal" or "crystalline form" refers to the crystal or the crystalline form being identified by the X-ray diffraction pattern shown herein. Those skilled in the art are able to understand that the X-ray powder diffraction pattern depend on the instrument conditions, the sample preparation and the purity of samples. The relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. Thus, it will be understood by those skilled in the art that a crystalline form of the present disclosure is not necessarily to have exactly the same X-ray diffraction pattern of the example shown herein. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

In some embodiments, Form CSVI of the present disclosure is pure and substantially free of any other crystalline forms. In the present disclosure, the term "substantially free" when used to describe a novel crystalline form, it means that the content of other crystalline forms in the novel crystalline form is less than 20% (w/w), specifically less than 10% (w/w), more specifically less than 5% (w/w) and furthermore specifically less than 1% (w/w).

In the present disclosure, the term "about" when referring to a measurable value such as weight, time, temperature, and the like, is meant to encompass variations of ±10%, ±5%, ±1%, ±0.5%, or even ±0.1% of the specified amount.

Unless otherwise specified, the following examples were conducted at room temperature. Said "room temperature" is not a specific temperature, but a temperature range of 10-30° C.

According to the present disclosure, Compound I used as raw materials include, but are not limited to solid (crystalline and amorphous), semisolid, wax, oil, liquid form or solution. Preferably, Compound I used as the raw material is a solid.

Raw materials of Compound I used in the following examples were prepared by prior arts, for example, the method disclosed in WO2020010068A1.

EXAMPLES

Example 1-2 Preparation of Form CSVI

Example 1

1.5801 g of Compound I was weighed into a glass bottle, followed by adding 25 mL of acetonitrile, and then stirred at room temperature for 4 days. The obtained solid was separated by filtration, and then blast dried the obtained solid at 40° C. for 15.5 h to obtain the crystal Form CSVI of the present disclosure.

The XRPD pattern of Form CSVI is substantially as depicted in FIG. 1 and the XRPD data are listed in Table 3.

Figure 2:
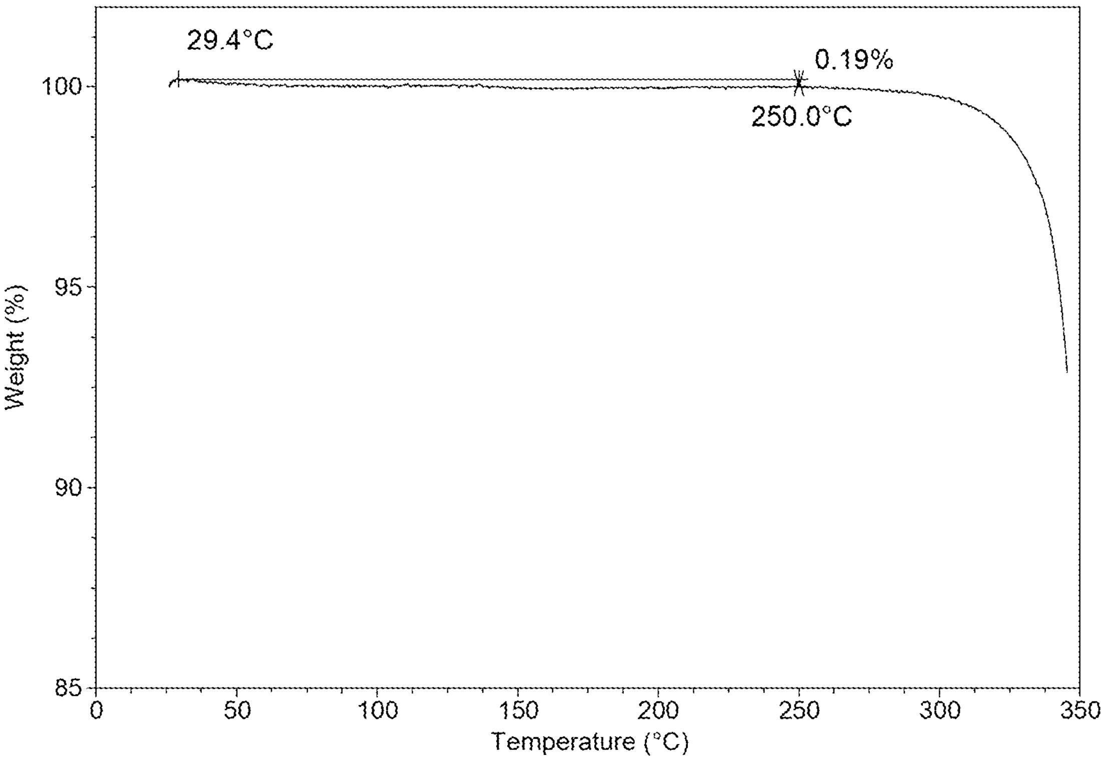
FIG. 2 shows a TGA curve of Form CSVI according to example 1

The TGA curve of Form CSVI is substantially as depicted in FIG. 2, which shows about 0.2% weight loss when heated to 250° C.

The $^{1}H$ NMR data of Form CSVI is: $^{1}H$ NMR (400 MHz, DMSO-d6) δ 13.28 (s, 1H), 12.23 (s, 1H), 7.79 (s, 2H), 7.44 (d, J=0.8 Hz, 1H), 3.04 (dq, J=13.5, 6.8 Hz, 1H), 1.20 (d, J=6.9 Hz, 6H).

Figure 3:
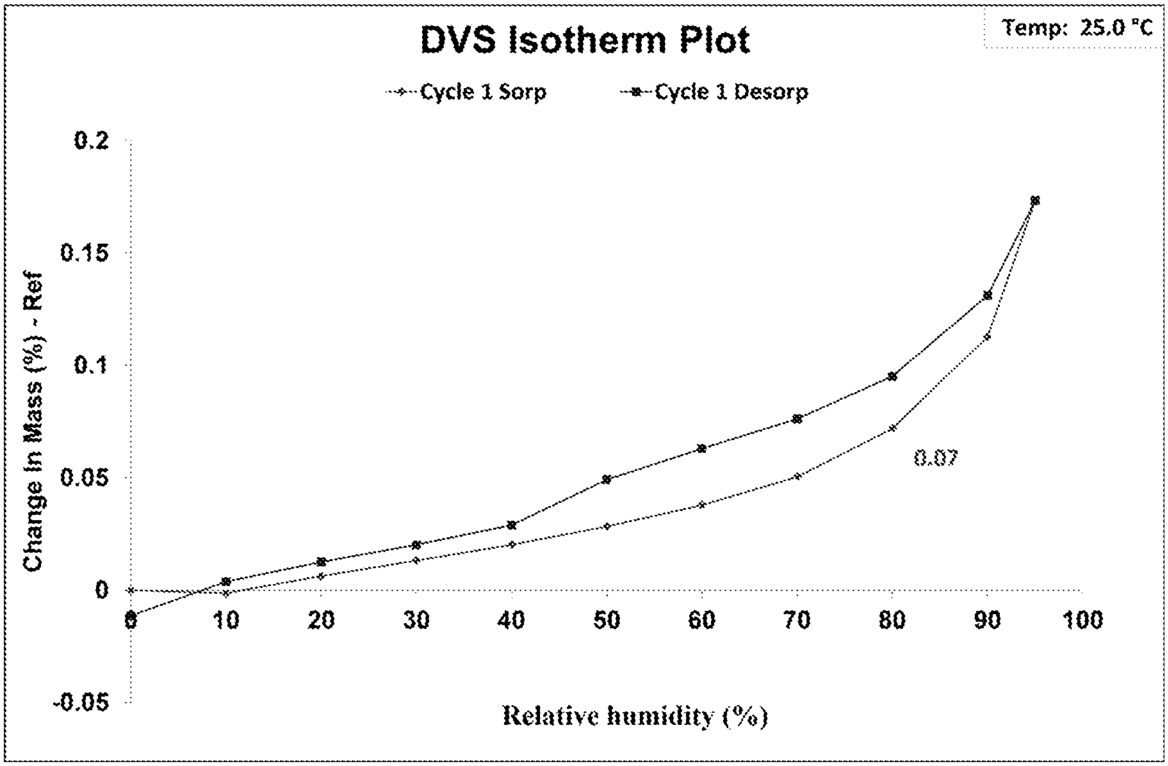
FIG. 3 shows a DVS plot of Form CSVI according to example 1

The DVS plot of Form CSVI is substantially as depicted in FIG. 3. The weight gain of Form CSVI at 25° C./80% RH is 0.07%, indicating that Form CSVI is non or almost non hygroscopic.

Figure 4:
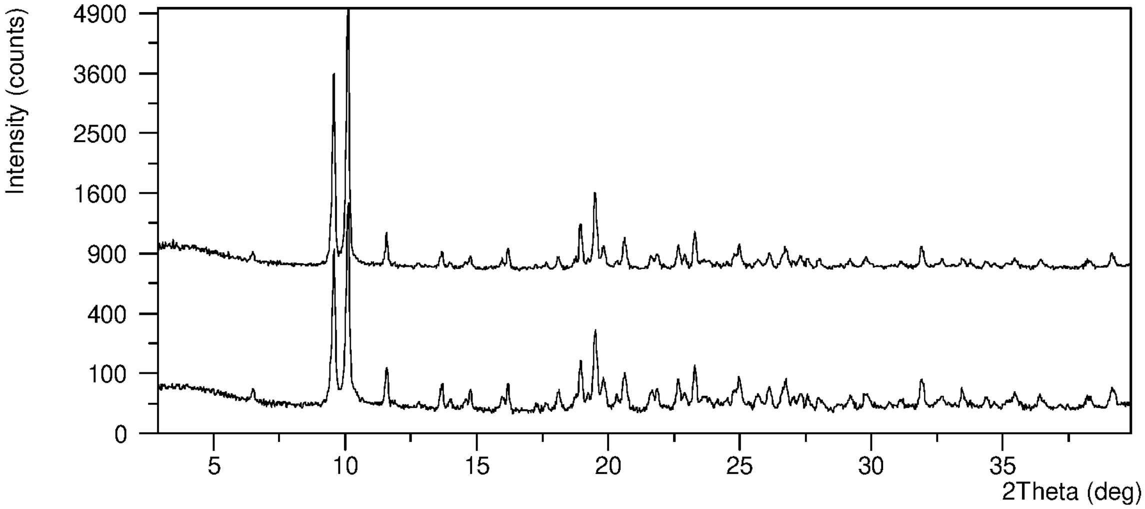
FIG. 4 shows an XRPD pattern overlay of Form CSVI before and after DVS test according to example 1 (top: before DVS, bottom: after DVS)

The XRPD pattern overlay of Form CSVI before and after DVS test as depicted in FIG. 4, indicating that the crystal form of Form CSVI does not change after DVS test.

TABLE 3

| 2θ (°) | d spacing (Å) | Relative intensity (%) |
|---|---|---|
| 6.49 | 13.62 | 2.06 |
| 9.57 | 9.25 | 65.84 |
| 10.11 | 8.75 | 100.00 |
| 11.58 | 7.65 | 7.89 |
| 12.77 | 6.93 | 0.88 |
| 13.68 | 6.48 | 3.39 |
| 13.98 | 6.33 | 0.91 |
| 14.75 | 6.00 | 2.41 |
| 16.19 | 5.48 | 4.32 |
| 17.64 | 5.03 | 1.13 |
| 18.10 | 4.90 | 2.23 |
| 18.94 | 4.68 | 10.63 |
| 19.50 | 4.55 | 19.67 |
| 19.81 | 4.48 | 4.75 |
| 20.33 | 4.37 | 1.63 |
| 20.61 | 4.31 | 7.02 |
| 21.62 | 4.11 | 2.74 |
| 21.86 | 4.07 | 2.96 |
| 22.66 | 3.92 | 4.89 |
| 22.91 | 3.88 | 2.66 |
| 23.29 | 3.82 | 8.60 |
| 23.72 | 3.75 | 1.44 |
| 24.14 | 3.69 | 0.98 |
| 24.80 | 3.59 | 3.03 |
| 24.98 | 3.57 | 4.96 |
| 25.69 | 3.47 | 1.87 |
| 26.12 | 3.41 | 3.40 |
| 21.86 | 4.07 | 2.96 |
| 22.66 | 3.92 | 4.89 |
| 22.91 | 3.88 | 2.66 |
| 23.29 | 3.82 | 8.60 |
| 23.72 | 3.75 | 1.44 |
| 24.14 | 3.69 | 0.98 |
| 24.80 | 3.59 | 3.03 |
| 24.98 | 3.57 | 4.96 |
| 25.69 | 3.47 | 1.87 |
| 26.12 | 3.41 | 3.40 |
| 26.75 | 3.33 | 4.17 |
| 27.31 | 3.27 | 2.57 |
| 27.57 | 3.24 | 1.94 |
| 28.01 | 3.19 | 1.85 |
| 29.19 | 3.06 | 1.72 |

TABLE 3-continued

| 2θ (°) | d spacing (Å) | Relative intensity (%) |
|---|---|---|
| 29.79 | 3.00 | 2.09 |
| 31.13 | 2.87 | 1.30 |
| 31.90 | 2.81 | 4.91 |
| 32.68 | 2.74 | 1.98 |
| 33.48 | 2.68 | 1.87 |
| 33.77 | 2.65 | 1.24 |
| 34.37 | 2.61 | 1.29 |
| 35.45 | 2.53 | 1.92 |
| 36.44 | 2.47 | 1.70 |
| 38.27 | 2.35 | 1.43 |
| 39.14 | 2.30 | 3.36 |

Example 2

22.0 mg of Compound I was weighed into a glass bottle, followed by adding 2.0 mL of the solvent mixture of acetonitrile and water (95:5, V:V), and then dissolved at 50° C., filtered, then the filtrate was stirred at −20° C. for 4 h. The obtained solid was separated by filtration, and then dried the obtained solid at 25° C. under a vacuum for 2 h to obtain the crystal Form CSVI of the present disclosure.

Figure 5:
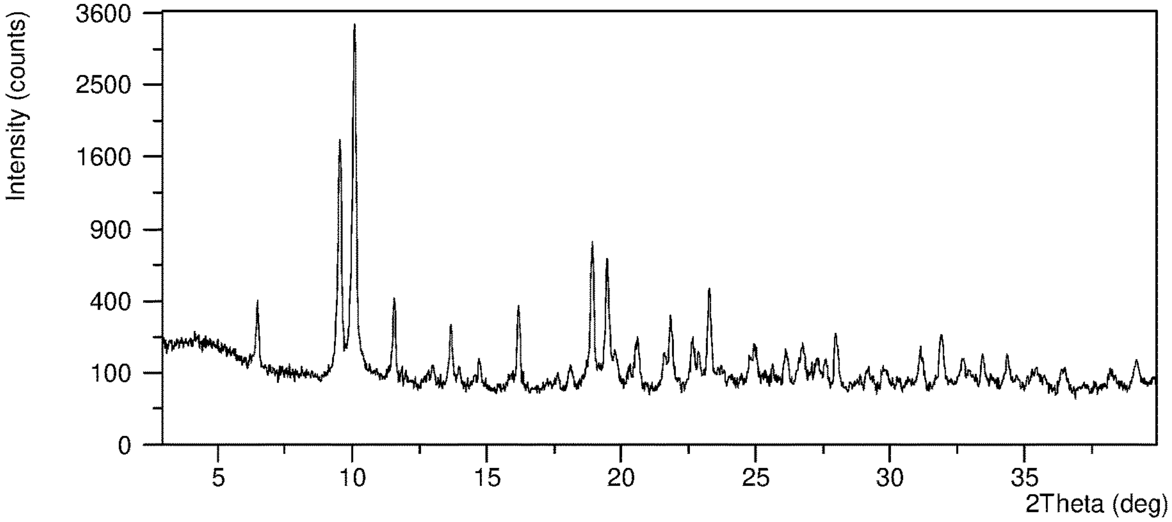
FIG. 5 shows an XRPD pattern of Form CSVI according to example 2

The XRPD pattern of Form CSVI is substantially as depicted in FIG. 5 and the XRPD data are listed in Table 4.

TABLE 4

| 2θ (°) | d spacing (Å) | Relative intensity (%) |
|---|---|---|
| 6.48 | 13.65 | 9.15 |
| 9.55 | 9.26 | 51.51 |
| 10.09 | 8.76 | 100.00 |
| 11.56 | 7.65 | 10.22 |
| 13.00 | 6.81 | 1.45 |
| 13.67 | 6.48 | 6.38 |
| 13.97 | 6.34 | 1.56 |
| 14.71 | 6.02 | 2.42 |
| 16.18 | 5.48 | 9.37 |
| 17.61 | 5.04 | 0.98 |
| 18.11 | 4.90 | 1.81 |
| 18.93 | 4.69 | 22.10 |
| 19.49 | 4.56 | 18.39 |
| 19.82 | 4.48 | 2.83 |
| 20.61 | 4.31 | 4.81 |
| 21.61 | 4.11 | 3.08 |
| 21.84 | 4.07 | 7.91 |
| 22.64 | 3.93 | 4.23 |
| 22.88 | 3.89 | 3.26 |
| 23.27 | 3.82 | 12.36 |
| 24.97 | 3.57 | 3.66 |
| 25.62 | 3.48 | 1.81 |
| 26.11 | 3.41 | 3.28 |
| 26.73 | 3.34 | 3.74 |
| 27.28 | 3.27 | 2.52 |
| 27.59 | 3.23 | 2.25 |
| 27.96 | 3.19 | 5.37 |
| 29.20 | 3.06 | 1.70 |
| 29.76 | 3.00 | 1.82 |
| 31.13 | 2.87 | 3.79 |
| 31.91 | 2.81 | 5.06 |
| 32.69 | 2.74 | 2.33 |
| 33.43 | 2.68 | 3.01 |
| 34.36 | 2.61 | 2.57 |
| 35.41 | 2.53 | 1.64 |
| 36.43 | 2.47 | 1.33 |
| 38.18 | 2.36 | 1.33 |
| 39.15 | 2.30 | 2.37 |

Example 3 Solubility of Form CSVI and Form I in the Prior Art

When solubility test is used to predict the in vivo performance of a drug, it is critical to simulate in vivo conditions as closely as possible. Simulated gastric fluid (SGF) can be used to simulate the condition in vivo and predict the effects of eating, thus solubility in this medium is closer to that in vivo. 15 mg of Form CSVI was suspended into 2.0 mL of SGF. After equilibrated for 1 h at 37° C., concentrations of the saturated solutions were measured by HPLC. The results are listed in Table 5.

TABLE 5

| Medium | Form I in the prior art | Form CSVI |
|---|---|---|
| | Solubility (mg/mL) | |
| SGF | 0.0011 | 0.0021 |

Note:
The solubility data of Form I in the prior art is quoted from WO2020010068A1

The results show that Form CSVI has a higher solubility after equilibrated in SGF for 1 h, and the solubility of Form CSVI is about 2 times that of Form I in the prior art.

Example 4 Hygroscopicity of Form CSVI and Form I in the Prior Art

Dynamic vapor sorption (DVS) analyzer was applied to evaluate the hygroscopicity of Form CSVI and Form I in the prior art with an appropriate amount. The weight gains at each relative humidity were recorded in a cycle of 0-95%-0 RH.

The DVS plot of Form CSVI is substantially as depicted in FIG. 3. The XRPD pattern overlay of Form CSVI before and after DVS test is substantially as depicted in FIG. 4.

The results show that the weight gain of Form CSVI at 25° C./80% RH is 0.07%. The weight gain of Form I in the prior art at 25° C./80% RH is 0.13%. The weight gain of Form I in the prior art is about 2 times that of Form CSVI.

Example 5 Physicochemical Stability of Form CSVI

Figure 6:
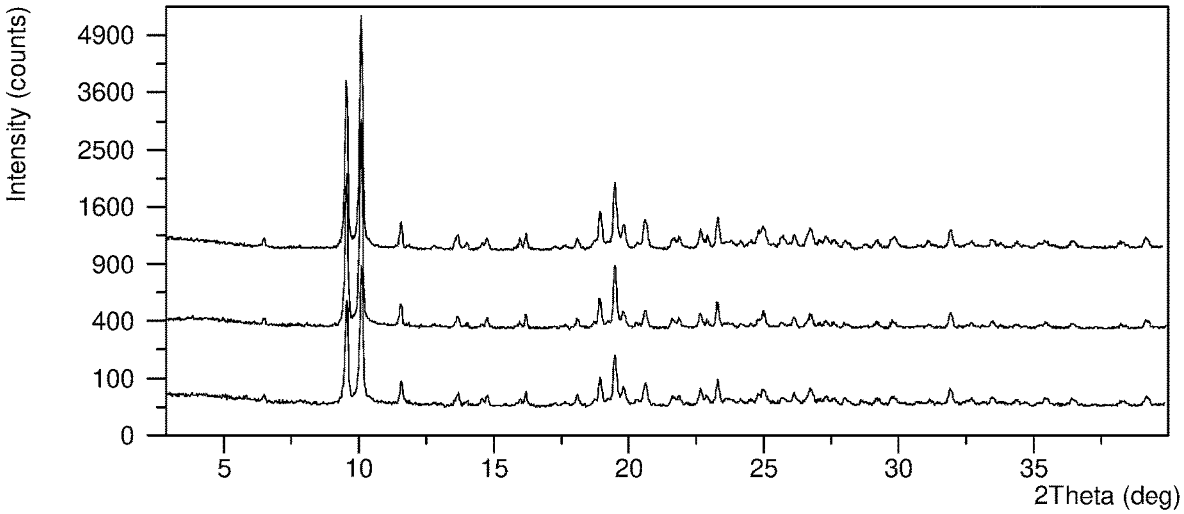
FIG. 6 shows an XRPD pattern overlay of Form CSVI before and after storage with different conditions (from top to bottom: initial, 25° C./60% RH for 6 months with open package, ° C./75% RH for 6 months with open package)
Figure 7:
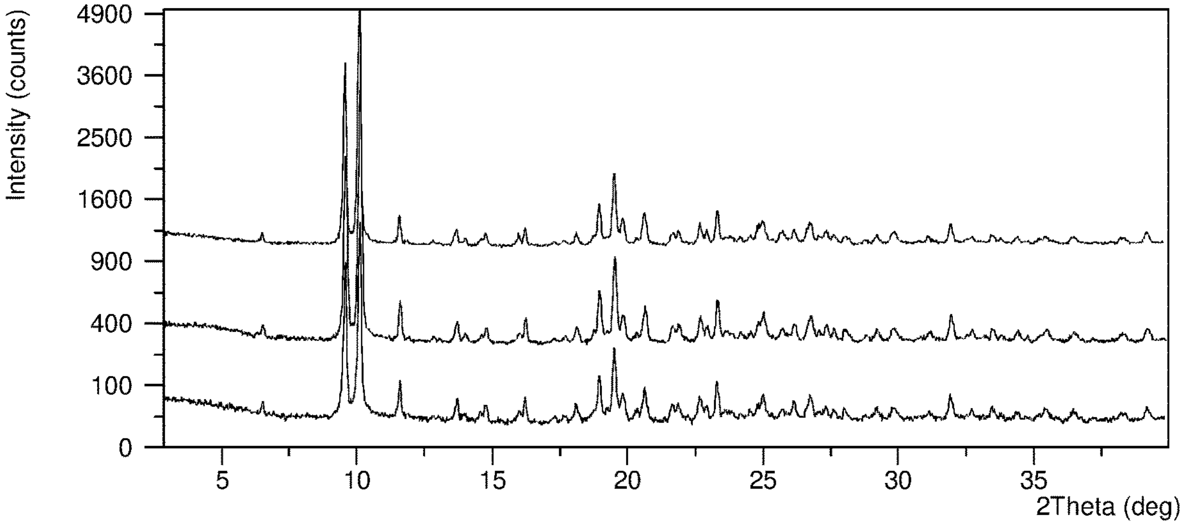
FIG. 7 shows an XRPD pattern overlay of Form CSVI before and after storage with different conditions (from top to bottom: initial, 25° C./60% RH for 6 months with sealed package, ° C./75% RH for 6 months with sealed package)

An appropriate amount of Form CSVI were stored under different conditions of 25° C./60% RH and 40° C./75% RH. Crystalline form and chemical purity were checked by XRPD and HPLC, respectively. The results are shown in Table 6, and the XRPD overlay are shown in FIG. 6 and FIG. 7.

TABLE 6

| Condition | Time | Solid Form | Purity |
|---|---|---|---|
| Initial | — | Form CSVI | 99.73% |
| 25° C./60% RH Open | 6 months | Form CSVI | 99.73% |
| 40° C./75% RH Open | 6 months | Form CSVI | 99.73% |
| 25° C./60% RH Sealed | 6 months | Form CSVI | 99.74% |
| 40° C./75% RH Sealed | 6 months | Form CSVI | 99.73% |

The results show that Form CSVI with open and sealed packaged kept stable for at least 6 months at 25° C./60% RH and 40° C./75% RH. Form CSVI has good stability under both long-term and accelerated conditions.

Example 6 Physical Stability of Form CSVI Upon Mechanical Force

Pressure Stability

Figure 8:
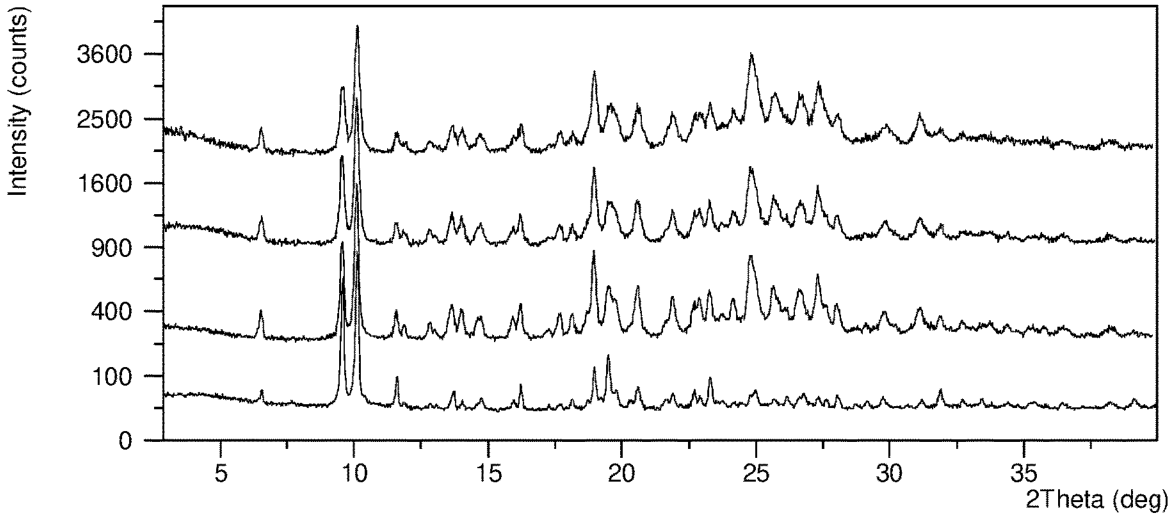
FIG. 8 shows an XRPD pattern overlay of Form CSVI with different pressure conditions (from top to bottom: 14 kN, 7 kN, 3 kN, initial)

ENERPAC manual tablet press was used for compression. 20 mg of Form CSVI were compressed into tablets under different pressures with the dies of a 16 mm round tooling. Crystalline form before and after tableting were checked by XRPD. The test results are shown in Table 7. The XRPD pattern overlay of Form CSVI before and after tableting is shown in FIG. 8.

TABLE 7

| Before tableting | Pressure | Solid form after tableting |
|---|---|---|
| Form CSVI | 3 kN | Form CSVI |
| | 7 kN | Form CSVI |
| | 14 kN | Form CSVI |

The results show that Form CSVI has good stability under different pressures.

Grinding Stability

Solid sample of Form CSVI was ground manually for 5 minutes in a mortar. Form CSVI remained stable before and after grinding.

Example 7 Flowability of Form CSVI and Form I in the Prior Art

Compressibility index is usually utilized to evaluate the flowability of powder or granules during the drug product process. Compressibility index test method is as follows: a certain amount of powder was added into a measuring cylinder and bulk volume was recorded. Then the powder was tapped to make it in the tightest state and the tapped volume was recorded.

The bulk density (ρ0), tapped density (ρf) were calculated and compressibility index was calculated according to c=(ρf−π0)/ρf.

Criteria of flowability according to ICH Q4B Annex 13 is shown in Table 8.

TABLE 8

| Compressibility index (%) | Flowability |
|---|---|
| ≤10 | Excellent |
| 11-15 | Good |
| 16-20 | Fair |
| 21-25 | Passable |
| 26-31 | poor |
| 32-37 | Very poor |
| >38 | Very, very poor |

The results show that the flowability of Form I in the prior art is very poor. The flowability of Form CSVI is superior to that of Form I in the prior art.

Example 8 Compressibility of Form CSVI and Form I in the Prior Art

ENERPAC manual tablet press was used for compression. 80 mg of Form CSVI and Form I in the prior art were weighed and added into the dies of a 16 mm round tooling, compressed at 10 KN manually, then stored at room temperature for 24 h until complete elastic recovery, diameter (D) and thickness (L) were tested with caliper. Hardness (H) was tested with an intelligent tablet hardness tester. Tensile strength of the powder was calculated with the following formula: T=2H/πDL. Under a certain force, the greater the tensile strength, the better the compressibility. The results are presented in Table 9.

TABLE 9

| Form | Thickness (mm) | Diameter (mm) | Hardness (N) | Tensile strength (MPa) |
|---|---|---|---|---|
| Form I in the prior art | 2.12 | 6.06 | 7.4 | 0.37 |
| Form CSVI | 2.05 | 6.06 | 13.4 | 0.69 |

The results indicate that Form CSVI has better compressibility compared with Form I in the prior art.

Example 9 Adhesiveness of Form CSVI and Form I in the Prior Art 30 mg of Form CSVI and Form I in the prior art were weighed and then added into the dies of Φ8 mm round tooling, compressed at 10 KN and held for 30 s. The punch was weighed and amount of material sticking to the punch was calculated. The maximum amount and average amount of material sticking to the punch during the compression were recorded. Detailed experimental results are shown in Table 10.

TABLE 10

| Form | Maximum amount (mg) | Average amount (mg) |
|---|---|---|
| Form I in the prior art | 0.30 | 0.25 |
| Form CSVI | 0.10 | 0.05 |

Test results indicate that amount sticking to the punch of Form I in the prior art is five times that of Form CSVI. The adhesiveness of CSVI is superior to the prior art form.

Example 10 Preparation of CSVI Drug Product

Figure 9:
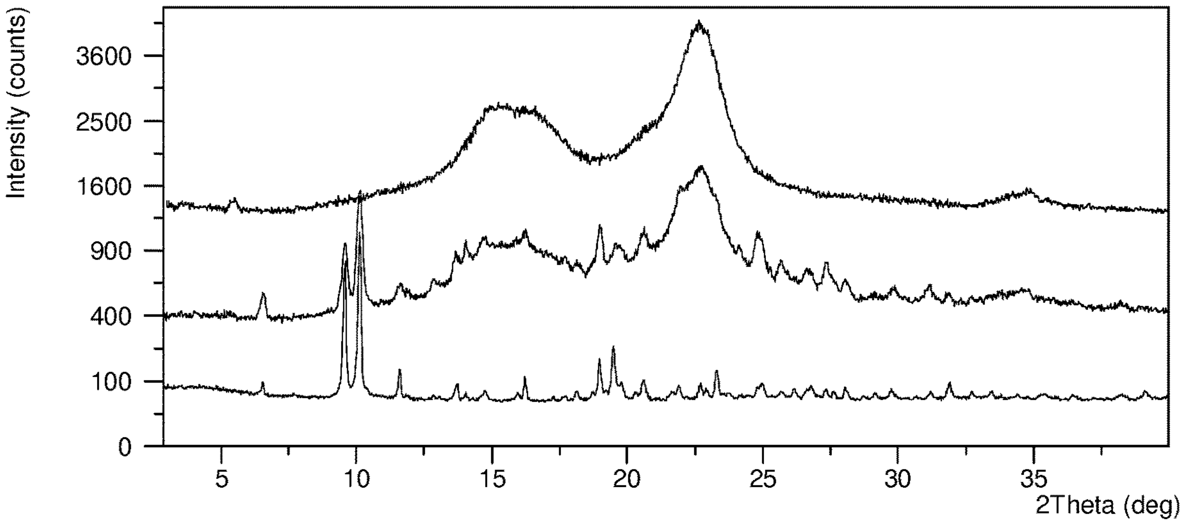
FIG. 9 shows an XRPD pattern overlay of Form CSVI before and after drug product process (from top to bottom: blank tablet, after drug product process, Form CSVI)

The formulation and preparation process of Form CSVI are shown in Table 11 and Table 12, respectively. The XRPD overlay of the samples before and after the formulation is shown in FIG. 9. The results showed that Form CSVI remained stable before and after the formulation process.

TABLE 11

| No. | Component | mg/unit | % (w/w) | Function |
|---|---|---|---|---|
| | Intra-granular | | | |
| 1 | Compound I | 32.0 | 32.0 | API |
| 2 | Microcrystalline Cellulose | 58.0 | 58.0 | filler |
| 3 | Povidone | 3.0 | 3.0 | Adhesive |
| 4 | Sodium Carboxymethyl Starch | 6.0 | 6.0 | Disintegrant |
| 5 | Magnesium stearate | 0.5 | 0.5 | Lubricant |
| | Extra-granular | | | |
| 6 | Magnesium stearate | 0.5 | 0.5 | Lubricant |
| | Total | 100.00 | 100.00 | N/A |

TABLE 12

| Stage | Procedure |
|---|---|
| Pre-blending | According to the formulation, No. 1-5 materials were weighed into an LDPE bag and blended for 2 mins; |
| Sifting | The mixture was pass through a 35-mesh sieve and then put in an LDPE bag and blended for 2 mins; |
| Simulation of dry granulation | Tableted by a single punch manual tablet press (type: ENERPAC; die: Φ20 mm round; tablet weight: 500 mg ± 100 mg; pressure: 5 ± 1 kN); The tablet was pulverized and sieved through a 20-mesh sieve, and put in an LDPE bag and blended for 2 mins; |
| Final mixing | Put the granule and No. 6 extra-granular into an LDPE bag and blended for 2 mins; |
| Tableting | Tableted by a single punch manual tablet press (type: ENERPAC; die: T 9*4 mm special; tablet weight: 100 mg; pressure: 5 kN) |

Example 11 Stability of Form CSVI in Drug Product

Figure 10:
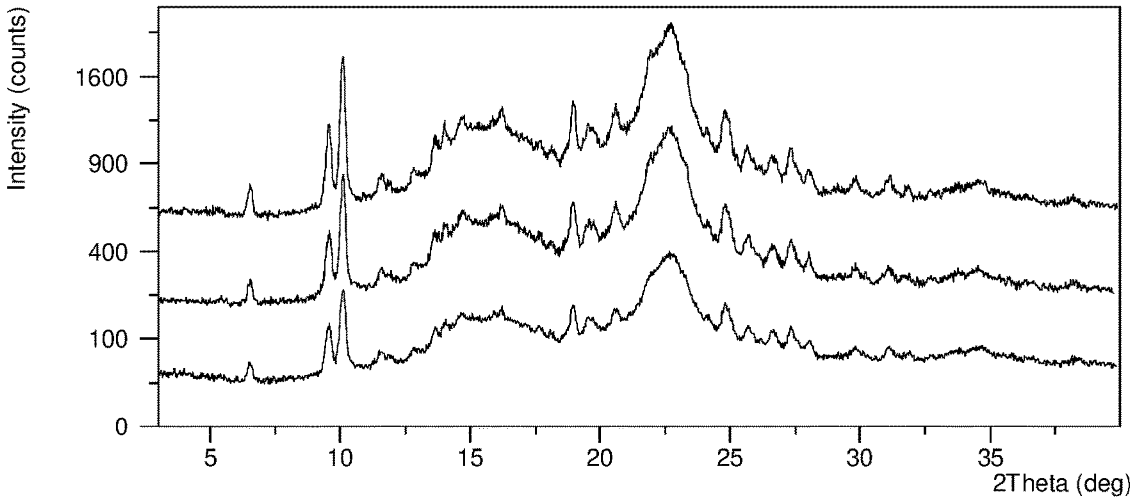
FIG. 10 shows an XRPD pattern overlay of Form CSVI drug product before and after storage with sealed conditions (from top to bottom: initial, 25° C./60% RH for 3 months, ° C./75% RH for 3 months)

The tablet of Form CSVI was packed in HDPE bottles with 1 g desiccant and stored under ° C./60% RH and 40° C./75% RH conditions. Crystalline form and impurity of the sample were tested to check the stability of Form CSVI drug product. The result is shown in Table 13. The XRPD overlay of the drug product of Form CSVI before and after the storage is shown in FIG. 10.

TABLE 13

| Condition | Purity change (%) | Solid form |
|---|---|---|
| Initial | N/A | Form CSVI |
| 25° C./60% RH sealed with 1 g desiccant one month | 0.08% | Form CSVI |
| 40° C./75% RH sealed with 1 g desiccant one month | 0.05% | Form CSVI |
| 25° C./60% RH sealed with 1 g desiccant three months | 0.03% | Form CSVI |
| 40° C./75% RH sealed with 1 g desiccant three months | 0.03% | Form CSVI |

The results indicate that Form CSVI drug product can keep stable under 25° C./60% RH and ° C./75% RH for at least 3 months.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A crystalline form of Compound I, wherein the crystalline form is an anhydrate and has an X-ray powder diffraction pattern comprising characteristic peaks at 2θ values of 9.6°±0.2°, 10.1°±0.2°, 13.7°±0.2°, 18.9°±0.2°, 20.6°±0.2°, and 31.9°±0.2 using CuKα radiation, Compound I

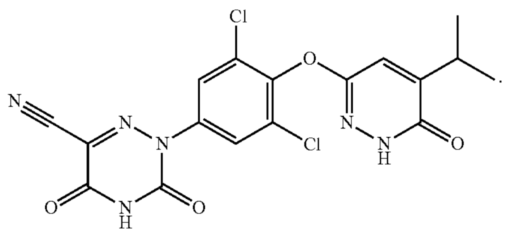

2. The crystalline form of Compound I according to claim 1, wherein the X-ray powder diffraction pattern comprises at least one characteristic peaks at 2θ values of 11.6°±0.2°, 19.5°±0.2°, and 23.3±0.2° using CuKα radiation.

3. The crystalline form of Compound I according to claim 1, wherein the X-ray powder diffraction pattern using CuKα radiation is substantially as depicted in FIG. 1.

4. A pharmaceutical composition, wherein said pharmaceutical composition comprises a therapeutically effective amount of crystalline form of Compound I according to claim 1, and pharmaceutically acceptable excipients.

5. A process for preparing the crystalline form of Compound I according to claim 1, wherein the process comprises:

(1) adding Compound I into a nitrile or a solvent mixture of nitrile and water, stirring, separating and drying to obtain the crystalline form; or (2) dissolving Compound I into a solvent mixture of a nitrile and water or a solvent mixture of a nitrile and an alcohol, filtering, cooling the filtrate, stirring to obtain solid, separating and drying to obtain the crystalline form.

6. The process according to claim 5, in method (1), wherein the nitrile is acetonitrile, a volume ratio of acetonitrile and water in the solvent mixture is 95:5; in method (2), wherein the nitrile is acetonitrile, the alcohol is isopropanol, a volume ratio of acetonitrile and water in the solvent mixture is 95:5, and a volume ratio of acetonitrile and isopropanol in the solvent mixture is 1:1.

7. The process according to claim 5, in method (1), wherein a stirring temperature is −20° C.-76° C., and a drying temperature is 10° C.-70° C.; in method (2), wherein a dissolving temperature is 40° C.-76° C., a cooling temperature is −20° C.-5° C., and a drying temperature is 10° C.-70° C.

8. The process according to claim 7, in method (1), wherein the stirring temperature is −20° C.-30° C., and the drying temperature is 10° C.-40° C.; in method (2), wherein the cooling temperature is −20° C., and the drying temperature is 10° C.-40° C.

9. A method for selectively activating THR-β, comprising administering the crystalline form of Compound I according to claim 1 to a subject in need thereof.

10. A method for treating NASH and HeFH, comprising administering the crystalline form of Compound I according to claim 1 to a subject in need thereof.

* * * * *